United States Patent
Shipp

(10) Patent No.: US 9,332,983 B2
(45) Date of Patent: May 10, 2016

(54) ABSORBABLE FASTENER FOR HERNIA MESH FIXATION

(75) Inventor: John I. Shipp, Atlantic Beach, FL (US)

(73) Assignee: Covidien LP, Mansfield, MA (US)

( * ) Notice: Subject to any disclaimer, the term of this patent is extended or adjusted under 35 U.S.C. 154(b) by 724 days.

(21) Appl. No.: 12/908,230

(22) Filed: Oct. 20, 2010

(65) Prior Publication Data

US 2011/0087240 A1    Apr. 14, 2011

Related U.S. Application Data

(63) Continuation of application No. 11/161,702, filed on Aug. 12, 2005, which is a continuation-in-part of application No. 10/907,834, filed on Apr. 18, 2005, now Pat. No. 8,114,099, which is a continuation-in-part of application No. 10/905,020, filed on Dec. 10, 2004, now abandoned, and a continuation-in-part of application No. 10/709,297, filed on Apr. 27, 2004, now Pat. No. 7,758,612.

(51) Int. Cl.
| | |
|---|---|
| *A61B 17/08* | (2006.01) |
| *A61B 17/064* | (2006.01) |
| *A61B 17/068* | (2006.01) |
| *A61F 2/00* | (2006.01) |

(52) U.S. Cl.
CPC ............ *A61B 17/064* (2013.01); *A61B 17/068* (2013.01); *A61B 2017/0648* (2013.01); *A61F 2/0063* (2013.01)

(58) Field of Classification Search
CPC ............ A61B 17/128; A61B 2017/0488; A61B 17/068; A61B 17/0642; A61B 2017/0648; A61B 2017/0649; A61B 17/0487; A61B 17/08; A61B 17/083; A61B 17/10; A61B 2017/044; A61B 2017/0409; A61B 17/0401; A61B 17/86; A61B 17/861; A61B 17/064; A61F 2/0063; A61F 2002/0068; A61F 2002/0072; A61F 2220/0016; A61F 2220/0041
USPC ......... 606/139, 151, 157, 158, 213, 295, 301, 606/305, 312, 316, 218, 285, 286, 288, 289
See application file for complete search history.

(56) References Cited

U.S. PATENT DOCUMENTS

| | | | |
|---|---|---|---|
| 298,427 A | 5/1884 | Stone | |
| 1,260,154 A | 3/1918 | Day | |

(Continued)

FOREIGN PATENT DOCUMENTS

| | | |
|---|---|---|
| CA | 2 527 778 A1 | 6/2004 |
| DE | 10 2010 015009 A1 | 10/2011 |

(Continued)

OTHER PUBLICATIONS

International Search Report corresponding to European Application No. EP 04 75 5078.5, mailed Jul. 2, 2008; 7 pages.
International Search Report corresponding to European Application No. EP 08 25 1988.5, mailed Oct. 17, 2008; 8 pages.
Extended International Search Report corresponding to European Application No. EP 08 02 1125.3, mailed Mar. 16, 2009; 6 pages.

(Continued)

*Primary Examiner* — David C Eastwood
*Assistant Examiner* — Erin Colello

(57) ABSTRACT

A method of forming and deploying an improved absorbable fastener for hernia mesh fixation is disclosed. The absorbable fastener of the present invention functions to securely fasten tough, non macro-porous, and relative inelastic mesh to soft tissue. The fastener is formed from co-polymers of lactide and glycolide.

23 Claims, 5 Drawing Sheets

(56) References Cited

U.S. PATENT DOCUMENTS

| | | | |
|---|---|---|---|
| 1,757,026 A * | 5/1930 | Tuttle | 74/377 |
| 3,528,466 A * | 9/1970 | Tracy | 81/431 |
| RE28,932 E * | 8/1976 | Noiles et al. | 227/19 |
| 4,204,541 A | 5/1980 | Kapitanov | |
| 4,756,653 A | 7/1988 | Berger | |
| 4,884,572 A | 12/1989 | Bays et al. | |
| 4,976,715 A | 12/1990 | Bays et al. | |
| 5,059,206 A | 10/1991 | Winters | |
| 5,080,665 A | 1/1992 | Jarrett et al. | |
| 5,129,906 A | 7/1992 | Ross et al. | |
| 5,163,343 A | 11/1992 | Gish | |
| 5,169,400 A | 12/1992 | Mühling et al. | |
| 5,203,864 A | 4/1993 | Phillips | |
| 5,259,398 A | 11/1993 | Vrespa | |
| 5,271,543 A * | 12/1993 | Grant et al. | 227/179.1 |
| 5,312,023 A | 5/1994 | Green | |
| 5,354,292 A | 10/1994 | Braeuer et al. | |
| 5,375,956 A | 12/1994 | Pennig | |
| 5,452,836 A * | 9/1995 | Huitema et al. | 227/176.1 |
| 5,458,638 A | 10/1995 | Kuslich et al. | |
| 5,487,500 A * | 1/1996 | Knodel et al. | 227/181.1 |
| 5,489,308 A | 2/1996 | Kuslich et al. | |
| 5,582,616 A * | 12/1996 | Bolduc et al. | 606/143 |
| 5,626,613 A | 5/1997 | Schmieding | |
| 5,643,320 A | 7/1997 | Lower et al. | |
| 5,728,116 A | 3/1998 | Rosenman | |
| 5,730,744 A | 3/1998 | Justin et al. | |
| 5,782,844 A * | 7/1998 | Yoon et al. | 606/139 |
| 5,830,221 A * | 11/1998 | Stein et al. | 606/157 |
| 5,891,146 A | 4/1999 | Simon et al. | |
| 5,906,616 A | 5/1999 | Pavlov et al. | |
| 5,954,722 A | 9/1999 | Bono | |
| 5,971,985 A | 10/1999 | Carchidi et al. | |
| 5,984,967 A | 11/1999 | Zdeblick et al. | |
| 6,030,162 A * | 2/2000 | Huebner | 411/413 |
| 6,096,060 A | 8/2000 | Fitts et al. | |
| 6,210,412 B1 | 4/2001 | Michelson | |
| 6,224,631 B1 | 5/2001 | Kohrs | |
| 6,241,771 B1 | 6/2001 | Gresser et al. | |
| 6,306,140 B1 | 10/2001 | Siddiqui | |
| 6,319,254 B1 | 11/2001 | Giet et al. | |
| 6,319,270 B1 | 11/2001 | Grafton et al. | |
| 6,371,988 B1 | 4/2002 | Pafford et al. | |
| 6,517,542 B1 * | 2/2003 | Papay et al. | 606/232 |
| 6,533,454 B1 | 3/2003 | Kaikkonen et al. | |
| 6,551,333 B2 * | 4/2003 | Kuhns et al. | 606/151 |
| 6,562,039 B1 | 5/2003 | Wang et al. | |
| 6,599,272 B1 * | 7/2003 | Hjertman et al. | 604/209 |
| 6,666,854 B1 | 12/2003 | Lange | |
| 6,706,046 B2 | 3/2004 | Orbay et al. | |
| 6,747,121 B2 | 6/2004 | Gogolewski | |
| 6,916,333 B2 * | 7/2005 | Schmieding et al. | 606/232 |
| 6,955,677 B2 | 10/2005 | Dahners | |
| 7,128,254 B2 * | 10/2006 | Shelton et al. | 227/181.1 |
| 7,204,847 B1 | 4/2007 | Gambale | |
| 7,371,244 B2 * | 5/2008 | Chatlynne et al. | 606/148 |
| 7,461,574 B2 * | 12/2008 | Lewis et al. | 81/57.37 |
| 7,527,639 B2 | 5/2009 | Orbay et al. | |
| 7,569,061 B2 | 8/2009 | Colleran | |
| 7,582,107 B2 | 9/2009 | Trail et al. | |
| 7,608,105 B2 | 10/2009 | Pavlov et al. | |
| 7,766,920 B2 * | 8/2010 | Ciccone et al. | 606/104 |
| 8,002,811 B2 * | 8/2011 | Corradi et al. | 606/300 |
| 8,292,933 B2 | 10/2012 | Zergiebel | |
| 8,323,314 B2 | 12/2012 | Blier | |
| 8,343,184 B2 | 1/2013 | Blier | |
| 8,414,627 B2 | 4/2013 | Corradi | |
| 8,465,520 B2 | 6/2013 | Blier | |
| 8,597,311 B2 | 12/2013 | Criscuolo et al. | |
| 8,728,120 B2 | 5/2014 | Blier | |
| 8,777,969 B2 | 7/2014 | Kayan | |
| 8,821,522 B2 | 9/2014 | Criscuolo et al. | |
| 8,821,557 B2 | 9/2014 | Corradi et al. | |
| 8,852,215 B2 | 10/2014 | Criscuolo et al. | |
| 2001/0004694 A1 | 6/2001 | Carchidi | |
| 2001/0007074 A1 | 7/2001 | Strobel et al. | |
| 2002/0004660 A1 | 1/2002 | Henniges et al. | |
| 2003/0009441 A1 * | 1/2003 | Holsten et al. | 707/1 |
| 2003/0036755 A1 | 2/2003 | Ginn | |
| 2003/0083661 A1 | 5/2003 | Orbay et al. | |
| 2003/0099102 A1 | 5/2003 | Duval | |
| 2003/0208275 A1 | 11/2003 | Michelson | |
| 2004/0030339 A1 | 2/2004 | Wack et al. | |
| 2004/0073218 A1 | 4/2004 | Dahners | |
| 2004/0098045 A1 | 5/2004 | Grafton et al. | |
| 2004/0127916 A1 | 7/2004 | Bolduc et al. | |
| 2004/0193165 A1 | 9/2004 | Orbay | |
| 2004/0204723 A1 | 10/2004 | Kayan | |
| 2004/0210227 A1 | 10/2004 | Trail et al. | |
| 2004/0243139 A1 * | 12/2004 | Lewis et al. | 606/104 |
| 2004/0254608 A1 | 12/2004 | Huitema et al. | |
| 2004/0260291 A1 | 12/2004 | Jensen | |
| 2005/0010226 A1 | 1/2005 | Grady et al. | |
| 2005/0070904 A1 | 3/2005 | Gerlach et al. | |
| 2005/0070958 A1 * | 3/2005 | Swayze et al. | 606/219 |
| 2005/0107796 A1 | 5/2005 | Gerlach et al. | |
| 2005/0136764 A1 | 6/2005 | Sherman | |
| 2005/0149027 A1 | 7/2005 | Campbell et al. | |
| 2005/0171562 A1 * | 8/2005 | Criscuolo et al. | 606/151 |
| 2005/0267478 A1 * | 12/2005 | Corradi et al. | 606/73 |
| 2006/0124688 A1 | 6/2006 | Racenet et al. | |
| 2006/0273135 A1 | 12/2006 | Beetel | |
| 2006/0291981 A1 | 12/2006 | Viola et al. | |
| 2007/0038220 A1 | 2/2007 | Shipp | |
| 2008/0039840 A1 | 2/2008 | Songer et al. | |
| 2008/0147113 A1 | 6/2008 | Nobis | |
| 2008/0188868 A1 | 8/2008 | Weitzner et al. | |
| 2008/0281336 A1 | 11/2008 | Zergiebel | |
| 2008/0312687 A1 | 12/2008 | Blier | |
| 2009/0118776 A1 | 5/2009 | Kelsch et al. | |
| 2009/0188965 A1 | 7/2009 | Levin | |
| 2010/0030262 A1 | 2/2010 | McLean et al. | |
| 2011/0022065 A1 | 1/2011 | Shipp | |
| 2011/0060349 A1 | 3/2011 | Cheng et al. | |
| 2011/0071578 A1 | 3/2011 | Colesanti | |
| 2011/0079627 A1 | 4/2011 | Cardinale | |
| 2011/0087240 A1 | 4/2011 | Shipp | |
| 2011/0295282 A1 | 12/2011 | Glick | |
| 2012/0059397 A1 | 3/2012 | Criscuolo et al. | |
| 2012/0109157 A1 | 5/2012 | Criscuolo et al. | |
| 2013/0018392 A1 | 1/2013 | Zergiebel | |
| 2013/0110088 A1 | 5/2013 | Wenchell | |
| 2013/0131700 A1 | 5/2013 | Criscuolo | |
| 2013/0197591 A1 | 8/2013 | Corradi | |
| 2014/0114329 A1 | 4/2014 | Zergiebel | |
| 2014/0121684 A1 | 5/2014 | Criscuolo | |
| 2014/0276967 A1 | 9/2014 | Fischvogt et al. | |
| 2014/0276969 A1 | 9/2014 | Wenchell et al. | |
| 2014/0276972 A1 | 9/2014 | Abuzaina et al. | |
| 2014/0316446 A1 | 10/2014 | Kayan | |
| 2014/0371765 A1 | 12/2014 | Corradi et al. | |
| 2015/0001272 A1 | 1/2015 | Sniffin et al. | |
| 2015/0005748 A1 | 1/2015 | Sniffin et al. | |
| 2015/0005788 A1 | 1/2015 | Sniffin et al. | |
| 2015/0005789 A1 | 1/2015 | Sniffin et al. | |
| 2015/0018847 A1 | 1/2015 | Criscuolo et al. | |
| 2015/0032130 A1 | 1/2015 | Russo | |
| 2015/0080911 A1 | 3/2015 | Reed | |

FOREIGN PATENT DOCUMENTS

| | | |
|---|---|---|
| EP | 0 121 362 A1 | 10/1984 |
| EP | 0 199 037 A2 | 10/1986 |
| EP | 0374088 A1 | 6/1990 |
| EP | 1 025 803 A1 | 8/2000 |
| EP | 1 293 168 A2 | 3/2003 |
| EP | 2005975 A2 | 12/2008 |
| EP | 2 055 241 A2 | 5/2009 |
| EP | 1908409 B1 | 12/2010 |
| EP | 2484294 A1 | 8/2012 |
| FR | 2 299 548 A1 | 8/1976 |
| FR | 2 377 796 A1 | 8/1978 |
| JP | 09149906 A | 6/1997 |
| WO | WO 98/11814 A2 | 3/1998 |

(56) References Cited

FOREIGN PATENT DOCUMENTS

| WO | 00/16701 A1 | 3/2000 |
|---|---|---|
| WO | WO 01/62136 A2 | 8/2001 |
| WO | WO 01/97677 A2 | 12/2001 |
| WO | WO 02/030296 A2 | 4/2002 |
| WO | WO 02/34140 | 5/2002 |
| WO | WO 02/091932 A1 | 11/2002 |
| WO | WO 03/034925 A2 | 5/2003 |
| WO | WO 03/049906 A1 | 6/2003 |
| WO | WO 03/103507 A2 | 12/2003 |
| WO | WO 03103507 A2 * | 12/2003 |
| WO | WO 2004/112841 | 12/2004 |
| WO | 2005004727 A1 | 1/2005 |
| WO | 2012/064692 A2 | 5/2012 |

OTHER PUBLICATIONS

Extended European Search Report corresponding to EP 14 15 9394.7, completed Apr. 16, 2014 and mailed Apr. 29, 2014; (8 pp).
Extended European Search Report corresponding to EP 14 15 8946.5, completed Jun. 20, 2014 and mailed Jul. 8, 2014; (9 pp).
Extended European Search Report corresponding to EP 14 17 8107.0, completed Nov. 24, 2014 and mailed Dec. 3, 2014; (5 pp).
Extended European Search Report corresponding to EP 14 17 4656.0, completed Jan. 16, 2015 and mailed Jan. 26, 2015; (7 pp).
Extended European Search Report corresponding to EP 14 18 4907.5, completed Jan. 12, 2015 and mailed Jan. 27, 2015; (9 pp).

* cited by examiner

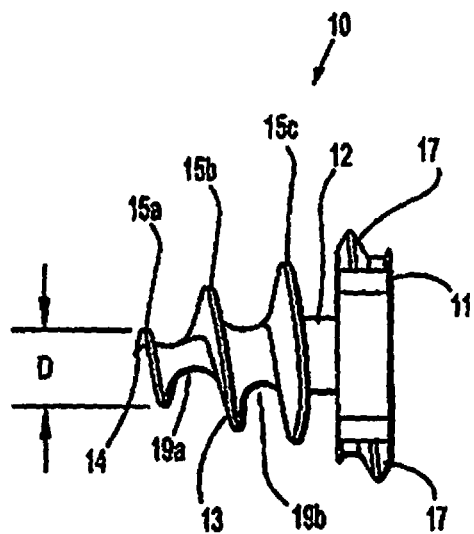
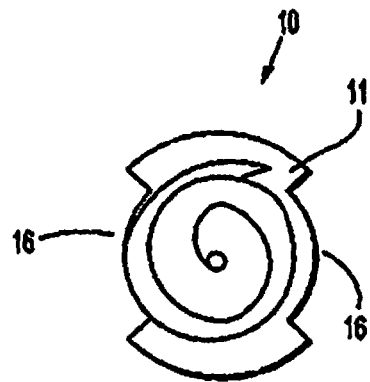
FIG. 1   FIG. 2
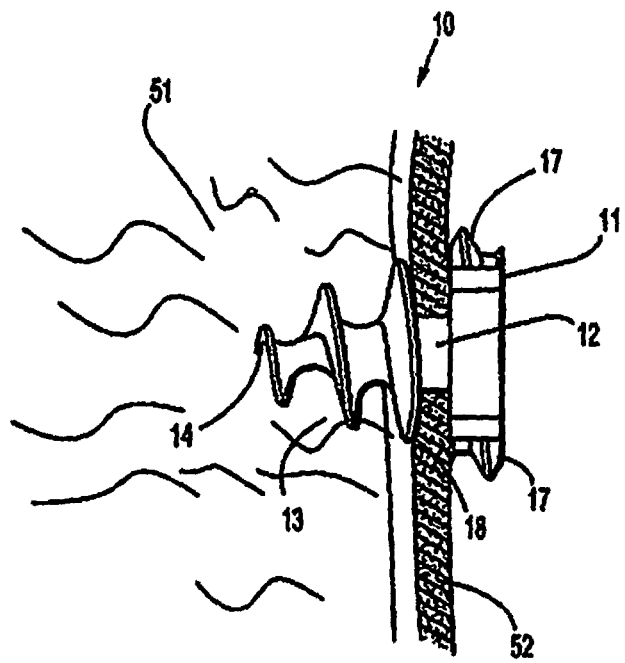
FIG. 3

ABSORBABLE FASTENER FOR HERNIA MESH FIXATION

CROSS REFERENCE TO RELATED APPLICATIONS

This application is a Continuation Application claiming the benefit of and priority to U.S. patent application Ser. No. 11/161,702, filed on Aug. 12, 2005, which is a Continuation-in-Part Application claiming the benefit of and priority to U.S. patent application Ser. No. 10/907,834, filed on Apr. 18, 2005 (now U.S. Pat. No. 8,114,099), which is a Continuation-in-Part Application claiming the benefit of and priority to U.S. patent application Ser. No. 10/905,020, filed on Dec. 10, 2004 (now abandoned), which is a Continuation-in-Part Application claiming the benefit of and priority to U.S. patent application Ser. No. 10/709,297, filed on Apr. 27, 2004 (now U.S. Pat. No. 7,758,612), the entire contents of each of which is incorporated by reference herein.

BACKGROUND OF THE INVENTION

This invention relates to surgical fasteners and their associated applicators, and more particularly, surgically fastening material to tissue and their method of use.

In laparoscopic repair of hernia fasteners have been used to attach repair mesh over the hernia defect so that bowel and other abdominal tissue are blocked from forming an external bulge that is typical of abdominal hernias. The role of the fasteners is to keep the mesh in proper position until tissue ingrowth is adequate to hold the mesh in place under various internal and external conditions. Adequate ingrowth usually takes place in 6-8 weeks. After that time the fasteners play no therapeutic role. Fixation fasteners comprise a mesh fixation feature, or head, a mesh-tissue interface section, and a tissue-snaring feature that holds the fastener in place under force developed inside or outside the body.

At present, there are a variety of surgical devices and fasteners available for the surgeon to use in endoscopic and open procedures to attach the mesh patch to the inguinal floor or abdominal wall. One such mesh attachment instrument uses a helical wire fastener formed in the shape of a helical compression spring. Multiple helical wire fasteners are stored serially within the 5 mm shaft, and are screwed or rotated into the mesh and the overlaid tissue to form the fastener for the prosthesis. A load spring is used to bias or feed the plurality of helical fasteners distally within the shaft. A protrusion extends into the shaft, while preventing the ejection of the stack of fasteners by the load spring, allows passage of the rotating fastener. U.S. Pat. Nos. 5,582,616 and 5,810,882 by Lee Bolduc, and U.S. Pat. No. 5,830,221 by Jeffrey Stein describe instruments and fasteners of this type.

U.S. Pat. Nos. 5,203,864 and 5,290,297 by Phillips describe two embodiments of a hernia fastener and delivery devices. One of the Phillips fasteners is formed in the shape of a unidirectional dart with flexible anchor members. The dart is forced through the mesh and into tissue by a drive rod urged distally by the surgeon's thumb. The anchor members are forced inward until the distal end of the dart penetrates the overlaid tissue and then the anchor members, presumably, expand outward without any proximal force on the dart thus forming an anchor arrangement. This requires an extremely forceful spring force generated by the anchor members. Multiple darts are stored in a rotating cylinder, much like a revolver handgun.

Phillips second fastener embodiment is a flexible H shaped device. The tissue penetrating means is a hollow needle containing one of the legs of the H. The H shape is flattened with the cross member and the other leg remaining outside the hollow needle owing to a longitudinal slot therein. A drive rod urged distally by the surgeon's thumb again delivers the fastener. The contained leg of the H penetrates the mesh and tissue. After ejection the fastener presumably returns to the equilibrium H shape with one leg below the tissue and one leg in contact with the mesh with the cross member penetrating the mesh and the tissue, similar to some plastic clothing tag attachments. Phillips depicts the installed device returning to the H shape but he fails to teach how to generate enough spring action from the device to overcome the high radial forces generated by the tissue.

A series of U.S. Pat. Nos. 6,572,626, 6,551,333, 6,447,524, and 6,425,900 and patent applications 200200877170 and 20020068947 by Kuhns and Kodel, all assigned to Ethicon, describe super elastic, or shape metal fasteners and a delivery mechanism for them. The fasteners are stored in the delivery device in a smaller state and upon insertion into the mesh and tissue, transitions to a larger anchor shaped state. The Ethicon fastener is delivered by an elaborate multistage mechanism through a hollow needle that has penetrated the mesh and the tissue. The hollow needle is then retracted to leave the fastener to change shape to a more suitable configuration for holding the mesh in place.

The primary problem associated with metallic fasteners is the formulation of permanent adhesions that attach themselves to the metallic implant. These adhesions can be of such a severity that fistulas are sometimes known to form and fasteners have been reported to migrate into the bowl and bladder. According to joels and others, in Surg Endosc (2005) 19: 780-785, adhesions form on titanium abdominal implants and more severely on shape metal implants.

Another major problem with these prior art fasteners is that the mesh is attached to body tissue in as many as 100 places for large ventral hernias. This results in a large quantity of metal remaining in the body as permanent implants, even though after the ingrowth phase the fasteners serve no useful purpose. Compounding this problem the distal ends of the fasteners are sharp pointed and thus pose a continued pain or nerve damage hazard.

One alternative to metallic fixation devices is bio-absorbable materials. These materials are degraded in the body by hydrolysis. This precludes permanent pain sites and minimizes or eliminates adhesions since after degradation the body metabolizes them as carbon dioxide and water. These materials require special attention to many design details, however, that is much more demanding than their counterparts in metallic fixation devices such as applicator tool design, sterilization processes, and packaging. Metallic tacks or fasteners provide structural strength that simplifies their insertion and since the materials, usually titanium or nickel-titanium alloys (shape metal), are chemical and radiation resistant and are very temperature tolerant many options are available to the designer that are not available for bio-absorbable materials.

The basic considerations of an effective mesh fixation applicator and absorbable fastener are the material strength, absorption time, the sterilization method, and packaging requirements, the ease of insertion of the fastener through the mesh and into the tissue, the ease of ejecting the fastener from the tool, the fixation strength of the fastener once implanted, the time required after insertion for the fastener to be degraded and metabolized by the body are all effected by the choice of fastener material, the geometry of the design, and the forming process.

Materials of appropriate strength are generally limited to synthetic materials. Currently, the U.S. FDA has cleared devices made from polyglycolide (PG), polylactide (PL), poly caprolactone, poly dioxanone, trimethylene carbonate, and some of their co-polymers for implant in the human body. These materials and their co-polymers exhibit a wide variation of properties. Flex modulus ranges from a few thousand to a few million PSI, tensile strength ranges from 1000 to 20,000 PSI, in vivo absorption times range from a few days to more than two years, glass transition temperatures range from 30-65 degrees centigrade, all with acceptable bio-responses. Unfortunately, however, the optimum values of each of these properties are not available in any one of these materials so that it is necessary to make performance tradeoffs.

Mechanical Properties

Most hernia mesh fixation devices are currently used in laparoscopic hernia repair. In general laparoscopic entry ports have been standardized to either 5 or 10 mm (nominal) diameter. In the case of prior art of metallic fixation devices 5 mm applicators are universally employed. Since it is not clear that the medical advantages of the use of absorbable fasteners would totally out weigh the disadvantages of moving to a 10 mm applicator it must be assumed that absorbable fasteners must also employ 5 mm applicators. Because of the lower strength of absorbable material this requirement imposes severe design constraints on both the applier and the fastener.

Implanted mesh fasteners are subjected to pull out forces from a number of sources. Non-porous mesh can be subjected to forces perpendicular to the abdominal wall by interabdominal pressure increases such as experienced during sneezing or coughing. These increased forces on the mesh are rather small however and non-existent for porous mesh. Most meshes in use today have a tendency to shrink after implant. The forces resulting from the shrinkage is, primarily, parallel to the abdominal surface and results in high shear and tensile forces on the fasteners. These forces can result in fixation failure. The fastener can fracture, separating the mesh holding feature from the tissue-snaring feature or it can pull out of the tissue owing to inadequate tissue snaring. Alternately, helical wire fasteners can unwind and offer little resistance to pull out. The shape metal anchor is inserted through a large needle hole and since it is flexible and very narrow in one dimension it can separate from the mesh owing to the mesh anchor arms bending upwards and threading back through the large insertion hole. The anchor often remains lodged in the tissue while separating from the mesh in this manner.

The strength and flexibility of the fastener material are of major importance in the design considerations of the applicator, particularly in the case of fasteners formed from polymers. Ory, et al (U.S. Pat. No. 6,692,506) teaches the use of L Lactic Acid polymer. Ory discloses adequate fixation strengths but the applicator device required to insert his fastener is necessarily 10 mm in diameter thereby causing the procedure to be more invasive than necessary. Ory further discloses a hollow needle with a large outside diameter, through which the fastener is inserted, that forms a rather large hole in the mesh and tissue to supply adequate columnar strength for penetration of the fastener. Entry holes of this size can give rise to multiple small hernias know as Swiss cheese hernias.

Absorption Time

There are two forms of PL, one synthesized from the d optical isomer and the other from the l optical isomer. These are sometimes designated DPL and LPL. A polymer with 50-50 random mixture of L and D is herein designated DLPL.

High molecular weight homo and co-polymers of PG and PL exhibit absorption times ranging from 1 month to greater than 24 months. Homo crystalline PG and PL generally require greater than 6 months to absorb and thus are not optimum materials for hernia mesh fixation. Amorphous co-polymers of PG and PL, on the other hand, typically degrade in less than 6 months and are preferably used in the present invention. For high molecular weight co-polymers of PG and PL the actual absorption time is dependent on the molar ratio and the residual monomer content. For a given monomer residual the absorption time varies from about 1 month to about 5 months as the molar content of DLPL increases from 50 to 85 percent with PG decreasing from 50 to 15 percent. Co-polymers of DLPL and PG in the molar range of 50 to 85 percent of DLPL are preferred for this invention. The geometry of the fastener also effects the absorption time. Smaller high surface area devices absorb faster.

The time required for the human body to react to the foreign body of the mesh for tissue ingrowth into the mesh is typically 10 days. However, mesh migration and mesh contraction can occur for more than two months if not adequately stabilized. Since fixation fasteners can impinge upon nerves and cause pain it is desirable for the fasteners to be absorbed as soon as possible after the tissue ingrowth and after the mesh is secure against migration or contraction. For most absorbable materials there is a difference between the time for loss of fixation strength and mass loss. Fixation strength decreases quicker than fastener mass owing to some degree of crystalline structure in the polymer. For these reasons the preferred absorption time for the current invention is 3-5 months after implant.

Absorption time can be effected by radiation sterilization. This must be taken into account when formulating the polymer if radiation sterilization is to be used. For large sterilization doses polymers may have to be formulated with longer than needed absorption times prior to radiation sterilization so that the desired absorption time is obtain after sterilization since radiation, generally, tends to reduce absorption time.

Temperature Effects

Glass transition temperature (Tg) is the temperature above which a polymer becomes soft, can loose its shape, and upon re-cooling can shrink considerably. Both crystalline and amorphous polymers exhibit glass transitions in a temperature range that depends on the mobility of the molecules, which is effected by a number of factors such as molecular weight and the amount of residual monomers. Glass transition temperatures range from about 43 to 55 degrees centigrade (deg. C.) for co-polymers of PG and DLPL. Where as 100% PG has a Tg of 35-40 deg. C. and 100% PL exhibits a Tg from 50-60 deg. C. Since the core temperature of the body can reach 40 degrees C. the preferred Tg for the material comprising the current invention is greater than 40 deg. C. In addition hernia mesh fasteners are often manufactured and shipped via surface transportation under uncontrolled, extreme heat conditions. Temperatures in commercial shipping compartments in the summer can exceed 60 degrees C. It is necessary to provide thermal protection in the packaging so that the fastener temperature does not exceed its Tg.

Sterilization and Packaging

Bio-absorbable polymers degrade when exposed to high humidity and temperature. Autoclaving cannot be used, for example. Most ethylene oxide (ETO) sterilization processes employ steam and high temperatures (above Tg) to obtain reasonable "kill" times for the bio-burden commonly found on the device. High doses of gamma radiation or electron beam radiation (E Bream), both accepted methods of sterilization for many devices, could weaken the mechanical properties of PG, PL and their co-polymers. It is therefore necessary during the manufacturing process of the fastener and its applicator to maintain cleanliness to a high degree such that the bio-burden of the components is small enough so that pathogens are adequately eradicated with less severe forms of sterilization.

Radiation doses above 25 kilogray (kgy) are known to lessen the mechanical strength of bio-absorbable polymers whereas some pathogens are known to resist radiation doses below 10 kgy. It is necessary, for the preferred embodiment of the present invention, during manufacturing to keep the pathogen count below a certain threshold to insure the accepted regulatory standards are met for radiation levels between 10 and 25 kgy.

In a second embodiment of the present invention it is necessary during manufacturing to keep the pathogen count below a certain threshold to insure the accepted regulatory standards are obtained for sterilization using a non-steam, low temperature, ethylene oxide (ETO) process below Tg of the fastener polymer.

Fasteners of the present invention must be carefully packaged to maintain adequate shelf life prior to use. Care must be taken to hermetically seal the device and to either vacuum pack, flood the package with a non-reactive dry gas prior to sealing, or to pack the device with a desiccant to absorb any water vapor since hydrolysis breaks down the backbone of the co-polymers.

ETO sterilization requires the gas to contact the device to be sterilized. Devices that are not humidity sensitive can be packaged in a breathable packaging material so that ETO can diffuse in, and after sterilization, diffuse out so that the device can be sterilized without unsealing the packaging. For the alternate embodiment of the present invention the device must be hermetically sealed after sterilization with ETO. Since gamma radiation and electron beam radiation sterilization can be accomplished through hermetically sealed packaging without disturbing the seal, either of these two sterilization processes is employed for the preferred embodiment of the present invention.

Ory, et al (U.S. Pat. No. 6,692,506), Criscuolo, et al (US application 20040092937), Phillips (U.S. Pat. Nos. 5,203,864 and 5,290,297), Kayan (U.S. application 20040204723), and Shipp (U.S. application Ser. Nos. 10/709,297, 10/905,020, and 10/907,834) have suggested the use of bio-absorbable materials for use as hernia mesh fixation devices to solve the problems associated with the permanency of metal implants. Ory, preferably, suggests forming the fixation device from LPL but the absorption time for LPL can exceed two years, much longer than optimum for hernia fixation devices since the lessening of pain depends on mass loss of the device. While Phillips and Kayan advocate the use of bio-absorbable material to form the fastener neither teach any details or methods for effectuating such a device. Criscuolo suggests the use of PG and PL with an absorption time of 2-3 weeks but does not disclose a method of forming the device that results in such an absorption time. In any respect, migration and contraction of the mesh has been documented to occur up to 8 weeks after implant. Loss of fixation after 2 to 3 weeks could well lead to hernia recurrence.

Hernia mesh such as PTFE based mesh manufactured by W. L. Gore is difficult to penetrate since the material is tough, non macro-porous, and relative inelastic. Attempts to penetrate these types of meshes with a puncture type applicator result in the mesh indenting into the tissue to a significant depth prior to penetration, especially for soft tissue. This indentation sometimes allows the tissue penetrator means, often a hollow needle, to penetrate through the abdomen wall and into the surgeon's hand, thus exposing the surgeon to potential hepatitis and AIDS viruses. The fastener of the present invention is equipped with screw threads that easily penetrate tough, non macro-porous, and relative inelastic mesh with a minimum of indentation. Once the threads are screwed through the mesh the underlying tissue is pull toward the mesh by the threads rather than push away from the mesh as is the case with puncture type devices.

Details of the method of manufacturing the improved fastener are herein provided.

What is needed then is an absorbable mesh fixation fastener and a method of forming an absorbable mesh fixation fastener that exhibits a known absorption time and that exhibits the mechanical properties adequate for the desired fixation strength and the required implant forces.

What is also needed is a method of packaging an absorbable mesh fixation device and the delivery device that minimizes the effects of high ambient shipping temperatures and humidity.

What is also needed is a method of sterilization of an absorbable mesh fixation fastener and its delivery device that has minimal effect on their physical properties, particularly the fastener.

What is further needed then is an absorbable mesh fixation fastener of improved geometry that easily penetrates tough, non macro-porous, and relatively inelastic mesh with minimal indentation to minimize the possibility of the fastener breaching the abdominal wall.

SUMMARY OF THE INVENTION

A method of producing and deploying a bio-absorbable hernia mesh fixation fastener exhibiting an in vivo absorption time between 1.5 and 13 months and its method of use is disclosed. A method of sterilization and a method of packaging the fastener to retain the critical physical properties of the fastener prior to implantation are also disclosed. The hernia mesh fixation device of the present invention is, preferably, injection molded using any of a variety of mole fractions of d, l-lactide and glycolide co-polymers, depending upon the desired absorption time, and mechanical properties. Preferably the mole ratio is 75-25 percent d, l lactide to glycolide yielding an absorption time after implant of 4-5 months and a glass transition temperature of 49 Deg. C. The modulus of elasticity of the preferred embodiment is 192,000 PSI and the tensile strength is 7200 PSI after injection molding at 150 Deg. C.

The fastener of the present invention comprises a head with a threaded portion and a slotted portion, a truncated, threaded tissue-snaring section that, upon rotation, easily penetrates tough, non macro-porous, and relative inelastic mesh and pulls underlying tissue toward the head of the fastener, firmly anchoring the mesh to the tissue and thus avoiding excessive indentation of the abdominal wall during deployment.

The fastener deliver device, or applier, of the present invention has a longitudinal axis, a proximal body, a handle, a rotator, a fastener retainer, a fastener advancer, a force reactor, and an fastener ejector.

Sterilization standards by the U.S. FDA allow radiation doses less than 25 kgy provided the bio-burden is below 1000 colony forming units (CFU). The components of the delivery device and the fasteners of the present invention are manufactured and assembled under clean room conditions such the bio-burden is well below 1000 CFUs. This allows gamma and E Beam sterilization with doses below the damage threshold of the preferred co-polymers of DLPL and PG, 25 kgy. Mechanical properties of the injected molded fastener of the present invention have been retested after dosing with 25 kgy E Beam. The same values of flex modulus and tensile strength were measured before and after dosing. Gamma or E Beam is the preferred sterilization process, however, an alternate embodiment comprises sterilization employing ethylene oxide without the use of steam and dosed at a temperature below the glass transition temperature.

For the preferred embodiment of the present invention the delivery device loaded with fasteners is first sealed into a vacuum formed tray with a breathable Tyvek (a registered trademark of DuPont) lid. This tray is then further hermetically sealed into a foil pouch. The foil pouch is then placed inside an insulated shipping container. The insulation is adequate to assure that the temperature of the fastener remains below 30 deg. C. after exposure to severe heat conditions sometimes experienced during shipping. Gamma or E Beam sterilization is accomplished by radiation through the shipping container.

In an alternate embodiment the sealed vacuum formed tray is placed into the hermetically sealed foil pouch after ETO sterilization. The ETO will penetrate the breathable lid. After the ETO process the device is sealed into the foil pouch and the pouch is placed into the thermally insulated container described above for shipping.

BRIEF DESCRIPTION OF THE DRAWINGS

FIG. 1 is a side view of the fastener according to the present invention.

FIG. 2 is the distal end view of the fastener according to the present invention.

FIG. 3 depicts the fastener fixating mesh to tissue.

DETAILED DESCRIPTION

Figure 4:
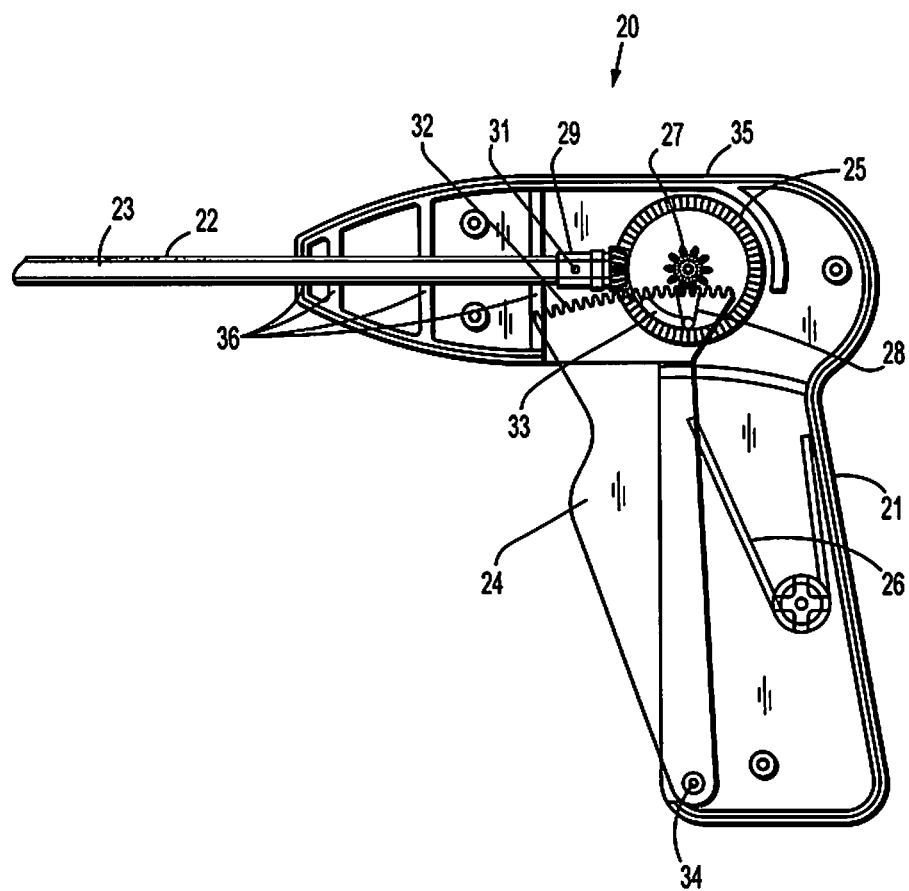
FIG. 4 is a cutaway view of the proximal end of the applier according to the present invention.

Turning now to FIGS. 1, 2 and 3, depictions of the fastener of the current invention, generally designated as 10. Fastener 10 may be a non-cannulated fastener that comprises three sections, head section 11, mesh retention section 12, and threaded tissue-snaring section 13. Head section 11 comprises two opposing head threads 17 and two opposing open or slotted sections 16. The distal surface of head section 11 is formed onto the proximal end of mesh retention section 12. The preferred maximum dimension of head 11 transverse to the longitudinal axis of fastener 10 is 5 mm.

Mesh retention section 12 may, alternately, be tapered or right-cylinder shaped or may be omitted, which would allow the proximal end of threaded tissue-snaring section 13 to abut the distal end of head section 11. Unlike the embodiment of fastener 10 with no mesh retention section 12, either the conical or cylindrical configuration mesh retention section 12 locks mesh 52 on to fastener 10 when mesh 52 is screwed past the proximal-most tissue-snaring thread 15c since there is no thread located in mesh retention section 12 that would allow mesh 52 to be unscrewed from fastener 10. Mesh retention section 12 is generally cylindrical or conical shaped with a dimension transverse to its longitudinal axis that is smaller than the transverse dimension of head 11 and the transverse dimension of proximal most tissue-snaring thread 15c. Preferably the dimension transverse to the mesh retention section 12 longitudinal axis is 1 and 1.5 mm and the dimension parallel to the longitudinal axis is preferably between 0.5 and 1.5 mm.

Threaded tissue-snaring section 13 comprises aggressive, auger-like threads peaks, 15a, 15b and 15c. Threads 13 spiral in either a right hand or left hand manner (here shown right hand) from the distal end of mesh retention section 12 to the distal surface 14 of fastener 10 with, preferably, three thread peaks 15a, 15b, and 15c and two thread roots 19 band 19a.

Figure 7A:
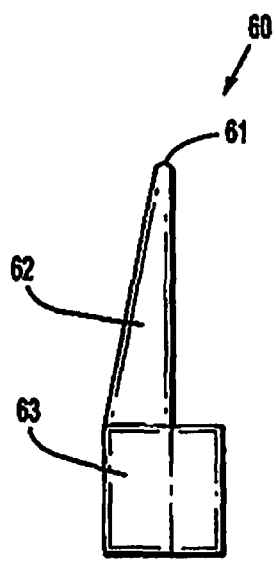
FIG. 7a is a side profile of fastener thread cutter.
Figure 7B:
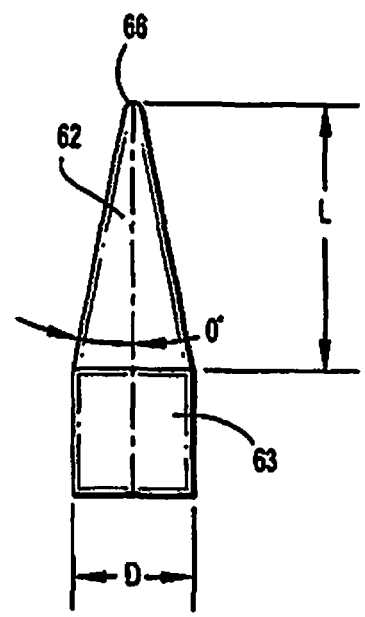
FIG. 7b is a front profile of fastener thread cutter.
Figure 8:
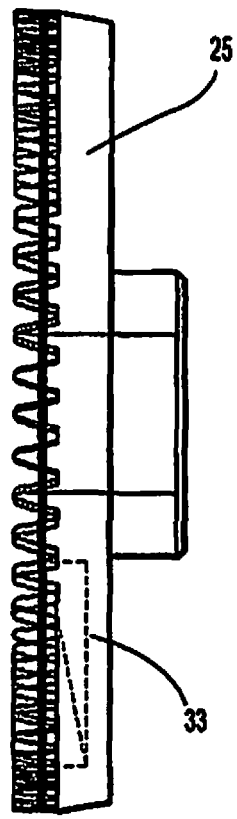
FIG. 8 depicts the side view of bevel gear with groove.

FIG. 8 depicts a preferred embodiment of a tool steel thread cutter 60 for cutting thread section 13. Cutter 60 comprises a mounting shank 63 of diameter D and cutter section 62. Tapering a length of cylinder with angle theta and then removing half the tapered material to the centerline of the cylinder as depicted in FIGS. 7a and 7b results in forming cutting section 62. Radii 61 and 66 preferably are ground on the tip of cutter section 62. Preferably, theta is 20 degrees, D is 4.8 mm, L is 5.8 mm and radii 61 and 63 are 0.5 mm.

Thread section 13 can be formed by securing, preferably, a cylinder of absorbable polymer material, 5 mm diameter in diameter to one rotating axis of a three-axis machine center. Cutter 60 is chucked into a spindle and rotated at a speed appropriate for cutting the material on to which thread section 13 is to be cut. The longitudinal axis of cutter 60 is perpendicular to the longitudinal axis of the cylinder. The distal tip of cutter 60 is initially positioned on the centerline of the cylinder at a distance X from the distal surface of the cylinder. The machine center is then programmed to translate cutter 60 away from the cylinder's axis, which is rotated about the longitudinal axis, and simultaneous to move the cutter proximal. By starting the cutter distal of the cylinder, but on the centerline, the auger-type thread section 13 are formed. Any partial threads that occupy the mesh retention section 12 are then milled out so that mesh retention section 12 is preferably circular in cross section. Preferably, X is set to 0.75 mm and the machine center axis parallel to the cylinder axis is translated at a rate five times the rate at which cutter 60 is translated perpendicular to the cylinder axis. Preferably the cylinder is rotated four revolutions as cutter 60 moves from the starting position to just short of the distal surface of head 11. This process forms threads as depicted in FIG. 1. A similar, but mirrored process, can be employed to form electrodes for burning a cavity into each half of an injection mold. Care must be taken to insure surface 14 is sharp to insure fastener 10 easily penetrates tough mesh material such as expanded PTFE. Fastener 10 is then completed by cutting the partial head threads 17 using process well know in the art.

First thread peak 15c is formed at the distal end of mesh retention section 12 and is smaller in dimensions transverse to the longitudinal axis than head section 11 and larger than mesh retention section 12 in dimensions transverse to the axis. The preferred transverse dimensions are 3.7 mm and 1.1 mm of the first thread peak 15c and the first root 19b respectively. The preferred transverse dimensions for second thread peak 15b and second thread root 19a are 2.9 mm and 0.4 mm respectively. The preferred transverse dimension of third thread peak 15a is 1.5 mm.

Distal surface 14 is the terminus of tissue-snaring section 13. Owing to the process described above threads 18 terminate distally prior to reaching an apex. The dimension D shown in FIG. 1 is the transverse dimension of the distal most thread 15a of threaded tissue-snaring section 13. D should be as large as design constraints will allow, preferably, greater than 1 mm. This geometry allows for ease of mesh penetration and minimizes indentation of the mesh into soft tissue as compared to a pointed distal end. A larger value of D, results in less pressure to cause indentation of tissue 51 and mesh 52, for a given distal force exerted on applier 20 by the surgeon.

Figure 5:
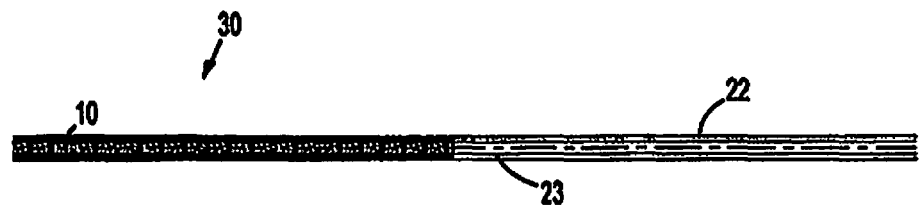
FIG. 5 is a cutaway view of the distal end of the applier according to the present invention.
Figure 6:
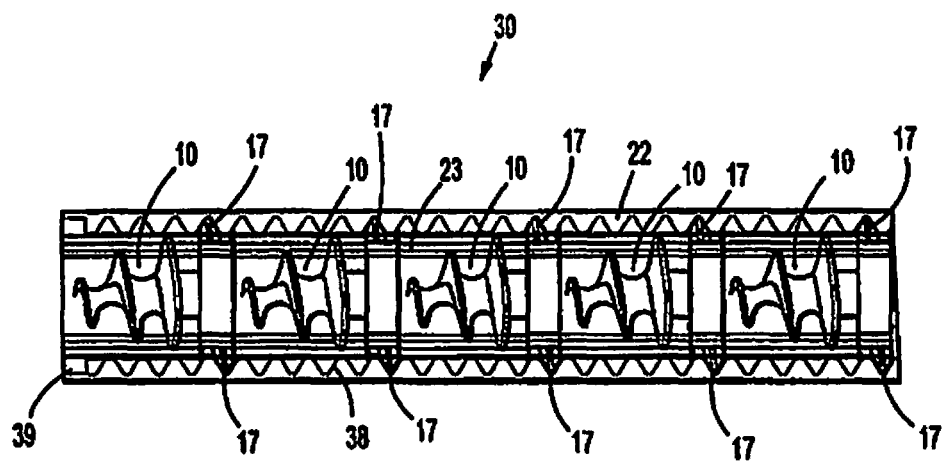
FIG. 6 is an enlargement of a cutaway view of the distal end of the applier according to the present invention.
Figure 9:
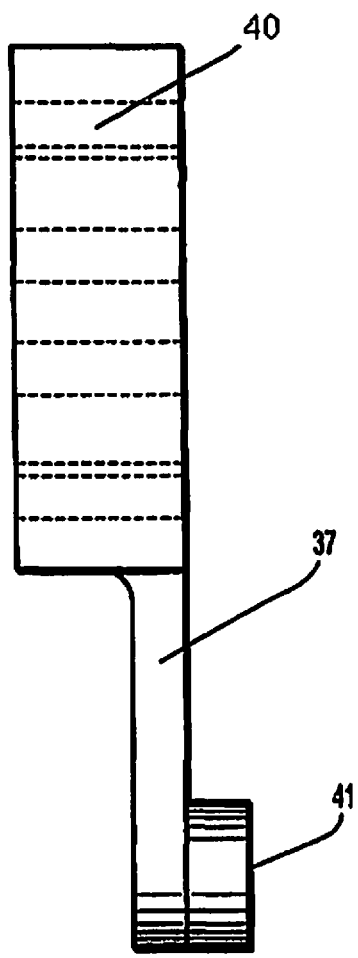
FIG. 9 is the anti-reversal drive device.

Turning now to Turning now to FIGS. 4, 5, and 6 depicting the delivery device, or applier, for mesh fastener 10, generally designated as 20. FIG. 4 is a cutaway view of the proximal end or body 35 of applier 20. Body 35 of applier 20 comprises handle 21, outer tube 22 stabilizer ribs 36, inner tube 23, trigger 24 with trigger gear 32 and trigger pivot 34 attached to handle 21, bevel gear 25, return spring 26, pinion gear 27, anti reversal drive 28, and bevel pinion gear 29. Pivot 34 is fixedly mounted to handle section 21 of body 35 and the axial for pinion 27 and bevel 25 is fixedly mounted to body 35. Drive 28 is fixed to pinion 27 owing to spline hub 40 that is fixedly attached to pinion 27. Drive 28 rotates bevel 25 owing to drive tooth 41 depicted in FIG. 9 mating into groove 33 in bevel 25 shown in FIG. 8.

FIG. 5 depicts the distal end 30 of applier 20 with twenty fasteners 10 loaded, ready for use.

FIG. 6 is cutaway view of an enlargement of the distal end 30 of applier 20 depicting the distal most five fasteners 10. Head threads 17 of fasteners 10 engage internal screw threads 38 in outer tube 22. The distal end of inner tube 23 is slotted to accept multiple fasteners 10, having two tines opposite the two slots, not shown because of the cutaway, that engage two fastener slots 16. Head threads 17 extend between the tines to engage outer tube threads 38. Rotation of inner tube 23 about its longitudinal axis rotates fasteners 10 and advances them distally owing to head threads 17 engagement with outer tube threads 38. In the preferred embodiment fasteners 10 are not in forced engagement with each other to avoid damage to distal tip 14 of fasteners 10.

In a preferred embodiment there are twenty-four tube threads 38 per inch, the overall length of fastener 10 is 0.203 inches, with five full turns of inner tube 23 advancing fasteners 10 0.208 inches. The distal end of outer tube 22 comprises counter bored 39 that preferably has a depth of 0.030 inches, which allows distal most fastener 10 to release from outer tube threads 38 in the last three quarters of a turn of a five turn actuation sequence in the application and ejection process, as will be detailed below.

Five embodiments of fastener 10 are described herein comprising four different molar ratios of DLPL and PG. The resins of the co-polymers in each case were prepared using well-known techniques of polymerization of cyclic dimmers. The molar percentages (M) of DLPL and PG were measured along with the residual monomer percentage (RM). After polymerization the resins were thoroughly dried. Fastener 10 was then injection molded in a standard micro-molding machine at 150 Deg. C. The transition glass temperature (Tg), the absorption time at 37 Deg. C. (to 20% of the original mass) (AT), the tensile strength (TS) and Young's modulus (YM) were then measured. Fastener 10 was then subjected to 25 kgy E Beam radiation and the tensile strength and Young's modulus re-measured. Standard techniques, well known by those skilled in the art, were employed in the measurements of each of the parameters. The results are shown below:

| | | | | | | | |
|---|---|---|---|---|---|---|---|
| | | | Case I | | | | |
| Parameter | M, DLPL, % | M, PG, % | RM, % | Tg, Deg. C. | AT, Months | TS, PSI | YN, PSI |
| | 100 | 0 | 2.1 | 49.4 | 13 | 6100 | 206,000 |

| | | | | | | | |
|---|---|---|---|---|---|---|---|
| | | | Case II | | | | |
| Parameter | M, DLPL, % | M, PG, % | RM, % | Tg, Deg. C. | AT, Months | TS, PSI | YN, PSI |
| | 85 | 15 | 2.1 | 49.7 | 5.8 | 7900 | 198,000 |

| | | | | | | | |
|---|---|---|---|---|---|---|---|
| | | | Case III | | | | |
| Parameter | M, DLPL, % | M, PG, % | RM, % | Tg, Deg. C. | AT, Months | TS, PSI | YN, PSI |
| | 75 | 25 | 1.6 | 49.1 | 4.3 | 7200 | 192,000 |

| | | | | | | | |
|---|---|---|---|---|---|---|---|
| | | | Case IV | | | | |
| Parameter | M, DLPL, % | M, PG, % | RM, % | Tg, Deg. C. | AT, Months | TS, PSI | YN, PSI |
| | 65 | 35 | 1.9 | 47.2 | 3.2 | 74000 | 190,000 |

| | | | | | | | |
|---|---|---|---|---|---|---|---|
| | | | Case V | | | | |
| Parameter | M, DLPL, % | M, PG, % | RM, % | Tg, Deg. C. | AT, Months | TS, PSI | YN, PSI |
| | 52 | 48 | 1.2 | 46.7 | 1.5 | 8100 | 188,000 |

In each case retesting the tensile strength and Young's modulus after subjecting the fastener 10 to 25 kgy E Beam radiation yielded results statistically indistinguishable from the values in the tables above.

To design an appropriate insulated shipping container the historical average daily temperatures over a "hot weather route" from Florida to Arizona were obtained from www.engr.udayton.edu/weather. Heat flux data were determined from the historical data resulting in an insulation requirement of 2.5 inches of Cellofoam (a registered trademark of Cellofoam of North America, Inc.) with a thermal R-value of 3.86 per inch of thickness. Fasteners 10 were then shipped over the route packed in the insulated container and the internal temperature of a un-air conditioned cargo space of a roadway common carrier was measured during a five-day trip from Jacksonville Fla. to Phoenix Ariz. from Sep. 9 till Sep. 14, 2004. The internal temperatures of the cargo space, Tc, and the internal temperature of the insulated container, Ti, containing fasteners 10 were recorded every 30 minutes. The minimum and maximum temperatures in the cargo space and the insulated container are shown below:

| | Day 1 | Day 2 | Day 3 | Day 4 | Day 5 |
|---|---|---|---|---|---|
| Maximum Tc Deg. C. | 37 | 34 | 29 | 48 | 50 |
| Minimum Tc Deg. C. | 24 | 18 | 15 | 27 | 27 |
| Maximum Ti Temperature, Deg. C. | 27 | 27 | 26 | 27 | 27 |

-continued

|  | Day 1 | Day 2 | Day 3 | Day 4 | Day 5 |
|---|---|---|---|---|---|
| Minimum Ti Temperature, Deg. C. | 24 | 26 | 21 | 24 | 24 |

Thus it is seen from the data above that the insulated shipping container is adequate for maintaining fastener 10 temperatures well below the glass transition temperature of 49 Deg. C. of the preferred co-polymer, 75/25 DLPL/PG, Case III above.

The preferred embodiment for the current invention is an injection molded fastener as depicted in FIG. 1 comprising 75% DLPL, 25% PG, sterilized with radiation, either gamma or E Beam, at 25 kgy and packaged first in a hermetically sealed pack and an insulated shipping container.

Applier Loading and Operation

Multiple fasteners 10 are loaded onto the tines of inner tube 23 head to tail with distal end 14 pointed distally. Fasteners 10 are rotationally orientated such that the tines of inner tube 23 engage head slots 16. The proximal end of the loaded inner tube assembly is inserted into the distal end of outer tube 22 until proximal-most fastener 10 encounters outer tube threads 38. The inner tube assembly is then rotated until the distal end of inner tube 23 is flush with or slightly recessed into outer tube 22. In this position the proximal end of inner tube 23 is proximal of the proximal end of outer tube 22. Near the proximal end of inner tube 23 a drill through hole perpendicular to the longitudinal axis is located to accept bevel pinion pin 31 for securing bevel pinion 29 to inner tube 23. The inner and outer tube assembly is then affixed into handle 21 with ribs 36 locking outer tube 22 against rotation or twisting in body 35. Two clamshell halves are ultrasonic welded or otherwise fastened together to form body 35.

Following sterilization loaded applier 20 is placed into a surgical field, usually through a 5 mm trocar, and the distal end of applier 20 is held firmly against mesh 52, which covers tissue 51. Outer tube threads 38 act as a force reactor to counter the distal force, generated by the screw-in process of the threaded tissue-snaring section 13, so that fasteners 10 are unable to move proximally. Outer tube threads 38 engaging head threads 17 also restrain fasteners 10 from falling out of the distal end of applier 20 under the influence of gravity, for example.

Trigger 24 is then rotated clockwise about pivot 34 causing pinion 27 to rotate counterclockwise. Drive tooth 41 is engaged in groove 33 and thus rotates bevel 25 counterclockwise. Bevel 25 causes bevel pinion 29 to rotate clockwise (in right hand sense, conventionally). The gear train is sized such that full movement of trigger 24 gear teeth 32 causes 5 revolutions of bevel pinion 29 and hence 5 revolutions of inner tube 23. This rotation of inner tube 23 rotates the stack of fasteners 10 five complete revolutions and advances them preferably 5.2 mm, the length of fastener 10, owing to head threads 17 and the pitch of outer tube threads 38, preferably 24 threads per inch.

As explained above rotation of inner tube 23 rotates fasteners 10. Distal surface 14 of distal most-fastener 10 engages and penetrates mesh 52 and threaded tissue-snaring section 13 screws into and draws tissue 51 and mesh 52 together. During the last three quarters of a rotation of the five revolutions head threads 17 of distal most fastener 10 enter into counter bore 39. Removal of the distal end 30 of applier 20 from mesh 52 releases distal-most fastener 10 and ejects it from applier 20. Mesh 52 is thus affixed to tissue 51. After the fastener screw-in process is complete trigger 24 is released, reset spring 26 returns trigger 24 with trigger gear 32 to its start, or home, position. This rotates pinion 27 and drive 28 clockwise. Flexible arm 37 allows drive tooth 41 to ride up out of groove 33 and rotate about the face of bevel 25 without bevel 25 rotating owing to greater friction of bevel 25 against its axial. Thus bevel 25, bevel pinion 29, inner tube 23, and fasteners 10 do not rotate during the return stroke of applier 20 during the reset process leaving the stack of fasteners 10 forward with each remaining fastener moved distally one fastener length. The features of applier 20 describe herein assures that the plurality of fasteners 10 progress distally one fastener length and do not move proximal during the return stroke. At the end of the return stroke drive tooth 41 has rotated 360 degrees on the face of bevel 25 and it snaps back into groove 33 and in position to drive bevel 5. Applier 20 is fully reset and ready for the deployment of the next fastener 10.

From the foregoing, it will be appreciated that the absorbable fastener of the present invention functions to securely fasten tough, non macro-porous, and relative inelastic mesh to tissue. The fastener of the present invention will disintegrate after the body has secured the mesh against migration and contraction. The absorbable fastener of the present invention can be sterilized so that mechanical properties are maintained and it can be shipped under severe temperature conditions with insulated packaging so that the glass transition temperature is not exceeded. It will also be appreciated that the absorbable fastener of the present invention may be utilized in a number of applications such as hernia repair, bladder neck suspension, and implant drug delivery systems.

While several particular forms of the invention have been illustrated and described, it will be apparent by those skilled in the art that other modifications are within the scope and spirit of the present disclosure.

What is claimed is:

1. A fastener applier apparatus comprising:
   a body;
   a trigger supported on the body;
   a non-cannulated threaded fastener including: a threaded head section; and a distal tissue snaring section;
   an actuator assembly transmitting motion from the trigger and including a rotary assembly supported in the body and being operatively connected to the trigger, the actuator assembly including: a spline hub;
   a flexible arm extending from the spline hub wherein the flexible arm rotates upon trigger actuation; and
   a drive tooth projecting from the flexible arm; and a gear rotatably supported in the body and being operatively associated with the drive tooth of the flexible arm, the gear defining a groove formed in a surface thereof for receipt of the drive tooth, the groove is configured such that rotation of the actuator assembly in a first direction causes the drive tooth to engage an end surface of the groove and transmit rotation to the gear, and such that rotation of the actuator assembly in a second direction, opposite the first direction, disengages the drive tooth from the groove of the gear and permits rotation of the actuator assembly independent of the gear;
   an inner tube including a slotted distal end configured to receive the threaded head section of the non-cannulated threaded fastener and an outer tube including screw threads configured to engage the threaded head section of the non-cannulated threaded fastener;
   wherein the inner and outer tubes support the non-cannulated threaded fastener and are configured to advance the non-cannulated threaded fastener distally away from the actuator assembly via rotation of the inner tube.

2. The fastener applier apparatus of claim 1, wherein at least part of the groove is defined by a ramp section to provide a sliding surface for disengagement of the drive tooth of the actuator assembly from the groove of the gear.

3. The fastener applier apparatus of claim 1, further including a drive pinion coupled to the inner tube, the drive pinion being operatively connected with the gear to rotate the inner tube.

4. The fastener applier apparatus of claim 3, wherein the gear associated with the drive tooth is configured to rotate the drive pinion and the inner tube a set number of full rotations with a single rotation thereof.

5. The fastener applier of claim 4, wherein the non-cannulated threaded fastener is located within the threaded outer tube of the fastener applier and engaged with the inner tube, the threaded outer tube being supported by the body, wherein:
   (1) the location of the threaded fastener is in the threaded outer tube, and
   (2) the configuration of the non-cannulated threaded fastener,
   being such that the set number of full rotations of the inner tube is required to fully expel the non-cannulated threaded fastener from the threaded outer tube.

6. The fastener applier apparatus of claim 1, further including a trigger gear extending from the trigger and being operatively connected to the actuator assembly, wherein, upon an actuation stroke, the trigger gear is configured to impart a full rotation of the gear associated with the drive tooth.

7. A fastener applier apparatus comprising:
a body;
a non-cannulated threaded fastener including: a threaded head section; and a distal tissue snaring section;
an outer tube extending from the body; the outer tube including screw threads configured to engage the threaded head section of the non-cannulated threaded fastener;
a drive rotatably supported in the outer tube and in the body; the drive including a slotted distal end configured to receive the threaded head section of the non-cannulated threaded fastener;
a trigger supported on the body; and
a gear system supported in the body and interconnecting the trigger and the drive, the gear system being configured to impart uni-directional rotation to the drive during any portion of a firing stroke of the trigger and during any portion of a return stroke of the trigger.

8. The fastener applier apparatus of claim 7, wherein the gear system includes a rotary ratchet system having a single tooth configured to engage a single catch of a rotary member supported in the body, wherein the tooth engages the catch upon a complete actuation of the trigger which transmits a rotation to the tooth relative to the rotary member.

9. The fastener applier apparatus of claim 7, wherein the gear system imparts a uni-directional forward rotation of the drive during at least a partial firing stroke of the trigger, and wherein the gear system inhibits a reverse rotation of the drive during any portion of a return stroke of the trigger.

10. The fastener applier apparatus of claim 7, wherein the trigger is pivotally mounted to the body to define a pivot end and a free end, the trigger defining a trigger gear along the free end, the trigger gear being operatively connected with the gear system to impart movement of at least a portion of the gear system during rotation of the trigger about the pivot end.

11. The fastener applier apparatus of claim 10, wherein the gear system includes:

a pinion gear operatively connected with the trigger gear and configured to rotate in response to the rotation of the trigger about the pivot end;
a bevel gear operatively connected with the pinion gear, the pinion gear being configured to rotate the bevel gear in a first direction in response to rotation of the trigger by the firing stroke;
a drive gear operatively connected with the bevel gear, the drive gear being coupled to the drive, the bevel gear being configured to rotate the drive gear to impart rotation of the drive in response to the rotation of the trigger by the firing stroke.

12. The fastener applier apparatus of claim 11, wherein the pinion gear has a flexible drive tooth projecting from a surface thereof and the bevel gear defining a groove formed in a surface thereof for receipt of the flexible drive tooth, the groove defining an end surface that is configured to engage with the drive tooth during rotation of the pinion gear in a first direction defined by the rotation produced during the firing stroke of the trigger, the groove configured to allow disengagement of the bevel gear with the drive tooth during rotation of the pinion gear in a second direction defined by the rotation produced during the return stroke of the trigger.

13. The fastener applier apparatus of claim 7, wherein the gear system is configured to rotate the drive a set number of full rotations with a single firing stroke of the trigger.

14. The fastener applier apparatus of claim 7, wherein the outer tube includes an outer surface and an inner surface, and the screw threads extending along a portion of the inner surface for engaging the threaded head section of the non-cannulated threaded fastener.

15. A fastener applier apparatus comprising:
a body;
a non-cannulated threaded fastener including: a threaded head section; and a distal tissue snaring section;
an outer tube extending from the body; the outer tube including screw threads configured to engage the threaded head section of the non-cannulated threaded fastener;
a drive rotatably supported in the outer tube and in the body; the drive including a slotted distal end configured to receive the threaded head section of the non-cannulated threaded fastener;
a trigger supported on the body;
a first actuation member supported in the body and engaged with the trigger, wherein any portion of a firing stroke of the trigger imparts a movement of the first actuation member in a first direction, and wherein any portion of a return stoke of the trigger imparts a movement of the first actuation member in a second direction; and
a second actuation member supported in the body and engaged with the first actuation member, wherein movement of the first actuation member in the first direction imparts a movement of the second actuation member in a third direction, and wherein movement of the first actuation member in the second direction imparts no movement to the second actuation member.

16. The fastener applier apparatus of claim 15, further including:
a trigger gear extending from the trigger;
wherein the first actuation member is a pinion gear rotatably supported in the body and being operatively connected with the trigger gear, the pinion gear including:

a spline hub;

a flexible arm extending from the spline hub; and a drive tooth projecting from the flexible arm; and wherein the second actuation member is a bevel gear rotatably supported in the body and being operatively associated with the drive tooth of the pinion gear, the bevel gear defining a groove formed in a surface thereof for receipt of the drive tooth, the groove is configured such that rotation of the pinion gear in a first direction causes the drive tooth to engage an end surface of the groove and transmit rotation to the bevel gear, and such that rotation of the pinion gear in a second direction, opposite the first direction, disengages the drive tooth from the groove of the bevel gear and permits rotation of the pinion gear independent of the bevel gear.

17. The fastener applier apparatus of claim 16, wherein at least part of the groove is defined by a ramp section to provide a sliding surface for disengagement of the drive tooth of the pinion gear from the groove of the bevel gear.

18. The fastener applier apparatus of claim 16, further including a drive pinion coupled to the drive, the drive pinion being operatively connected with the bevel gear to rotate the drive.

19. The fastener applier apparatus of claim 18, wherein the bevel gear is configured to rotate the drive pinion and the drive a set number of full rotations with a single rotation of the bevel gear.

20. The fastener applier of claim 19, wherein the location of the non-cannulated threaded fastener is in the outer tube and the configuration of the non-cannulated threaded fastener is such that the set number of full rotations of the drive is required to fully expel the non-cannulated threaded fastener from the outer tube.

21. The fastener applier apparatus of claim 16, wherein the trigger gear is configured to impart a full rotation of the bevel gear during the actuation stroke.

22. The fastener applier apparatus of claim 15, wherein the outer tube includes an outer surface and an inner surface, and the screw threads extending along a portion of the inner surface for engaging the threaded head section of the non-cannulated threaded fastener.

23. The fastener applier apparatus of claim 15, wherein the first actuation member is configured such that the firing stroke causes advancement of the non-cannulated threaded fastener distally within the outer tube.

* * * * *